US009551010B2

(12) United States Patent
Van der Loo et al.

(10) Patent No.: US 9,551,010 B2
(45) Date of Patent: Jan. 24, 2017

(54) METHODS OF IMPROVING RETROVIRAL TITER IN TRANSFECTION-BASED PRODUCTION SYSTEM USING EUKARYOTIC CELLS

(71) Applicant: Children's Hospital Medical Center, Cincinnati, OH (US)

(72) Inventors: Johannes Van der Loo, Loveland, OH (US); Lilith Reeves, Indianapolis, IN (US)

(73) Assignee: Children's Hospital Medical Center, Cincinnati, OH (US)

( * ) Notice: Subject to any disclaimer, the term of this patent is extended or adjusted under 35 U.S.C. 154(b) by 488 days.

(21) Appl. No.: 13/946,746

(22) Filed: Jul. 19, 2013

(65) Prior Publication Data

US 2013/0302898 A1 Nov. 14, 2013

Related U.S. Application Data

(63) Continuation of application No. 12/928,302, filed on Dec. 6, 2010, now abandoned.

(60) Provisional application No. 61/267,008, filed on Dec. 4, 2009.

(51) Int. Cl.
*C12N 15/64* (2006.01)
*C12N 15/86* (2006.01)
*C12N 15/63* (2006.01)
*C12N 15/85* (2006.01)

(52) U.S. Cl.
CPC .............. *C12N 15/86* (2013.01); *C12N 15/63* (2013.01); *C12N 15/85* (2013.01); *C12N 2740/15043* (2013.01); *C12N 2830/48* (2013.01)

(58) Field of Classification Search
CPC ..... C12N 15/85; C12N 15/63; C12N 15/8673; C12N 15/867
See application file for complete search history.

(56) References Cited

U.S. PATENT DOCUMENTS

| | | | |
|---|---|---|---|
| 6,524,851 | B1 | 2/2003 | Ellis |
| 7,276,340 | B1 | 10/2007 | Ballantyne et al. |
| 8,318,690 | B2 | 11/2012 | Collard et al. |
| 2006/0292599 | A1 | 12/2006 | Ritz et al. |
| 2007/0066548 | A1 | 3/2007 | Nagel |
| 2009/0156534 | A1 | 6/2009 | Lisowski et al. |
| 2011/0294114 | A1 | 12/2011 | Van Der Loo et al. |

OTHER PUBLICATIONS

Costa et al (Curret Protocols in Stem Cell Biology, pp. 1C.1.1-.1c. 1.7, Published on line Apr. 2008).*

Aiuti A, et al., "Correction of ADA-SCID by stem cell gene therapy combined with nonmyeloablative conditioning" Science, 2002, 296:2410-2413.
Aiuti A, et al., "Immune reconstitution in ADA-SCID after PBL gene therapy and discontinuation of enzyme replacement," Nat Med, 2002; 8: 423-425.
Aiuti A, et al., "Gene therapy for immunodeficiency due to adenosine deaminase deficiency," N Engl J Med 2009, 360(5):447-458.
Aker M, et al., "Extended core sequences from the cHS4 insulator are necessary for protecting retroviral vectors from silencing position effects". Hum Gene Ther, 2007, vol. 18 pp. 333-343.
Anson DS, and Fuller M."Rational development of a HIV-1 gene therapy vector," J Gene Med, 2003, 5: 829-838.
Arumugam PI, et al., "Improved human beta-globin expression from self-inactivating lentiviral vectors carrying the chicken hypersensitive site-4 (cHS4) insulator element," Mol Ther, 2007, 15: 1863-1871.
Arumugam, P., et al., "The 3' Region of the Chicken Hypersensitive Site-4 Insulator Has Properties Similar to Its Core and Is Required for Full Insulator Activity," PLoS ONE, 2009, vol. 4(9), pp. e6995.
Baskurt OK, et al., "Blood rheology and hemodynamics," Semin Thromb Hemost, 2003, 29(5):435-450.
Baudin F, et al., "Functional sites in the 5' region of human immunodeficiency virus type 1 RNA form defined structural domains," J Mol Biol ,1993, 229: 382-397.
Baum C, et al., "cis-Active elements of Friend spleen focus-forming virus: from disease induction to disease prevention," Acta Haematol,1998, 99:156-164.
Baum C. et al.,"Side effects of retroviral gene transfer into hematopoietic stem cells," Blood, 2003, 101:2099-2114.
Bell A, et al., "The establishment of active chromatin domains," Cold Spring Harb Symp Quant Biol, 1998, 63: 509-514.
Bell AC, et al., "The protein CTCF is required for the enhancer blocking activity of vertebrate insulators," Cell, 1999, 98: 387-396.
Bell, AC, and Felsenfeld, G, "Stopped at the border: boundaries and insulators," Curr Opin Genet Dev,1999, 9: 191-198.
Bell AC, et al., "Insulators and boundaries: versatile regulatory elements in the eukaryotic" Science, 2001, 291: 447-450.
Bender MA, et al., "A majority of mice show long-term expression of a human beta-globin gene after retrovirus transfer into hematopoietic stem cells," Mol Cell Biol, 1989; 9: 1426-1434.
Benhamida S, et al., "Transduced CD34_cells from adrenoleukodystrophy patients with HIV-derived vector mediate long-term engraftment of NOD/SCID mice," Mol Ther, 2003, 7(3):317-324.
Berkhout, B, et al., "Structural features in the HIV-1 repeat region facilitate strand transfer during reverse transcription," RNA, 2001, 7: 1097-1114.
Bernaudin F, et al., "Long-term results of related myeloablative stem-cell transplantation to cure sickle cell disease," Blood, 2007, 110(7):2749-2756.

(Continued)

*Primary Examiner* — Deborah Crouch
*Assistant Examiner* — Magdalene Sgagias
(74) *Attorney, Agent, or Firm* — Wolf, Greenfield & Sacks, P.C.

(57) ABSTRACT

The invention relates to methods of improving titer in transfection-based bioreactor culture production or transfection-based production systems using eukaryotic cells.

5 Claims, 2 Drawing Sheets

(56) References Cited

OTHER PUBLICATIONS

Berthold E, Maldarelli F, "cis-acting elements in human immunodeficiency virus type 1 RNAs direct viral transcripts to distinct intranuclear locations," J Virol, 199, 70: 4667-4682.
Biffi A, et al., "Gene therapy of metachromatic leukodystrophy reverses neurological damage and deficits in mice," J Clin Invest, 2006, 116:3070-3082.
Blouin MJ, et al., "Genetic correction of sickle cell disease: insights using transgenic mouse models," Nat Med, 2000, 6(2):177-182.
Brandt S, et al., "Rev proteins of human and simian immunodeficiency virus enhance RNA encapsidation," PLoS Pathog, 2007, 3: e54.
Brooks DA, et al., "Glycosidase active site mutations in human alpha-L-iduronidase," Glycobiology, 2001, 11:741-750.
Brown, PO, et al., "Correct integration of retroviral DNA in vitro," Cell, 1987, 49: 347-356.
Brule, F, et al., "In vitro evidence for the interaction of tRNA(3)(Lys) with U3 during the first strand transfer of HIV-1 reverse transcription," Nucleic Acids Res, 2000, 28: 634-640.
Buchman AR, Berg P, "Comparison of intron-dependent and intron-independent gene expression," Mol Cell Biol, 1988, 8: 4395-4405.
Buchschacher GL, Jr., "Panganiban AT. Human immunodeficiency virus vectors for inducible expression of foreign genes," J Virol, 1992, 66: 2731-2739.
Bukrinsky, MI, et al., "Active nuclear import of human immunodeficiency virus type 1 preintegration complexes," Proc Natl Acad Sci U S A, 1992, 89: 6580-6584.
Bushman FD, "Retroviral integration and human gene therapy," J Clin Invest, 2007, 117:2083-2086.
Butler, SL, et al., "A quantitative assay for HIV DNA integration in vivo," Nat Med, 2001, 7: 631-634.
Carr JM, et al., "Effect of deletion and the site of insertion in double copy anti-tat retroviral vectors: viral titers and production of anti-tat mRNA," Arch Virol, 2001, 146: 2191-2200.
Cavazzana-Calvo M, et al., "Gene therapy of human severe combined immunodeficiency (SCID)-X1 disease," Science, 2000, 288: 669-672.
Cavazzana-Calvo M, et al., "Hematopoietic stem cell gene therapy trial with lentiviral vector in X-linked adrenoleukodystrophy" Blood (ASH Annual Meeting Abstracts), 2008, (suppl)112, Abstract 821.
Challita, P., et al., "Lack of expression from a retroviral vector after transduction of murine hematopoietic stem cells is associated with methylation in vivo," Proc Natl Acad Sci, 1994, vol. 91(7), pp. 2567-2571.
Chang AH, et al., "Stem cell-derived erythroid cells mediate long-term systemic protein delivery," Nat Biotechnol, 2006, 24:1017-1021.
Chang AH and Sadelain M, "The genetic engineering of hematopoietic stem cells: the rise of lentiviral vectors, the conundrum of the ltr, and the promise of lineage-restricted vectors," Mol Ther, 2007, 15:445-456.
Chang DD and Sharp PA, "Messenger RNA transport and HIV rev regulation," Science, 1990, 249: 614-615.
Chang JC, et al, "A 36-base-pair core sequence of locus control region enhances retrovirally transferred human beta-globin gene expression," Proc Natl Acad. Sci USA, 1992, 89: 3107-3110.
Charache S, et al., "Hydroxyurea-induced augmentation of fetal hemoglobin production in patients with sickle cell anemia," Blood, 1987, 69(1):109-116.
Chasis JA and Mohandas N, "Erythroblastic islands: niches for erythropoiesis," Blood, 2008, 112:470-478.
Chung JH, et al., "Characterization of the chicken beta-globin insulator," Proc Natl Acad Sci U S A, 1997, 94: 575-580.
Coffin JM, "Retroviridae and their replication," in: Fields BN, "Fields Virology," 2 ed. ( New York, Raven Press, 1990), pp. 1437-1500.

Cone RD, et al, "Regulated expression of a complete human beta-globin gene encoded by a transmissible retrovirus vector," Mol Cell Biol, 1987, 7: 887-897.
Crusselle-Davis VJ, et al., "Antagonistic regulation of beta-globin gene expression by helix-loop-helix proteins USF and TFII-I" Mol Cell Biol, 2006, 26: 6832-6843.
Cuddapah S, et al., "Global analysis of the insulator binding protein CTCF in chromatin barrier regions reveals demarcation of active and repressive domains," Genome Res, 2009, 19: 24-32.
Cui Y, et al., "Contributions of viral splice sites and cis-regulatory elements to lentivirus vector function," J Virol 1999, 73: 6171-6176.
Darbari DS, et al., "Circumstances of death in adult sickle cell disease patients," Am J Hematol, 2006, 81(11):858-863.
Davis H, et al., "National trends in the mortality of children with sickle cell disease, 1968 through 1992," Am J Public Health, 1997, 87(8):1317-1322.
Dull T, et al., "A third-generation lentivirus vector with a conditional packaging system," J Virol, 1998, 72: 8463-8471.
Dzierzak E., et al., "Lineage-specific expression of a human B-globin gene in murine bone marrow transplant recipients reconstituted with retrovirus-transduced stem cells," Nature, 1988, 331: 35-41.
Ellis J, "Silencing and variegation of gammaretrovirus and lentivirus vectors," Hum Gene Ther, 2005, 16:1241-1246.
Elnitski L, et al., "Conserved E boxes function as part of the enhancer in hypersensitive site 2 of the beta-globin locus control region. Role of basic helix-loop-helix proteins," J Biol Chem, 1997, 272: 369-378.
Emery, DW, et al., "Development of virus vectors for gene therapy of beta chain hemoglobinopathies: flanking with a chromatin insulator reduces gamma-globin gene silencing in vivo," Blood, 2002, 100: 2012-2019.
Evans-Galea, et al., "Supression of clonal dominance in cultured human lymphoid cells by addition of 5' cHS4 insulator to a lentiviral vector," Molecular Therapy, 2006, 13: S405.
Evans-Galea MV, et al., "Suppression of clonal dominance in cultured human lymphoid cells by addition of the cHS4 insulator to a lentiviral vector," *Mol Ther*, 2000, 15: 801-809.
Fabry ME, et al., "Second generation knockout sickle mice: the effect of HbF," Blood, 2001, 97(2):410-418.
Favaro JP, et al., "Effect of Rev on the intranuclear localization of HIV-1 unspliced RNA," Virology, 1998, 249: 286-296.
Felber BK, et al., "rev protein of human immunodeficiency virus type 1 affects the stability and transport of the viral mRNA," *Proc Natl Acad Sci U S A*, 1989, 86: 1495-1499.
Felsenfeld et al., "Chromatin boundaries and chromatin domains," Cold Spring Harb Symp Quant Bioi, 2004, vol. 69, pp. 245-250.
Fischer, A., et al., "LMO2 and gene therapy for severe combined immunodeficiency," N Engl J, 2004, 350:2526-2527.
Fischer U, et al., "Evidence that HIV-1 Rev directly promotes the nuclear export of unspliced RNA," EMBO J, 1994, 13: 4105-4112.
Fitzhugh CD, et al., "Late effects of myeloablative bone marrow transplantation (BMT) in sickle cell disease (SCD)," Blood, 2008, 111(3):1742-1743, author reply 1744.
Franco RS, et al., "Time-dependent changes in the density and hemoglobin F content of biotin-labeled sickle cells," J Clin Invest, 1998, 101(12):2730-2740.
Gaspar HB, et al., "Successful reconstitution of immunity in ADA-SCID by stem cell gene therapy following cessation of PEG-ADA and use of mild preconditioning," Mol Ther, 2006, 14:505-513.
Gelinas, C, and Temin, HM , "The v-rel oncogene encodes a cell-specific transcriptional activator of certain promoters," Oncogene, 1988, 3: 349-355.
Geminard C, et al., "Reticulocyte maturation: mitoptosis and exosome release," Biocell, 2002, 26:205-215.
Gerasimova TI, et al., "A chromatin insulator determines the nuclear localization of DNA," Mol Cell, 2000, 6: 1025-1035.
Giralt, S. "Reduced-intensity conditioning regimens for hematologic malignancies: what have we learned over the last 10 years?" *Hematology*, 2005, 2005:384-9.
Grande, A, et al., "Transcriptional targeting of retroviral vectors to the erythroblastic progeny of transduced hematopoietic stem cells," Blood, 1999, 93: 3276-3285.

(56) References Cited

OTHER PUBLICATIONS

Grewal S, et al., "Continued neurocognitive development and prevention of cardiopulmonary complications after successful BMT for I-cell disease: a long-term follow-up report," Bone Marrow Transplant, 2003, 32:957-960.
Grubb JH, et al., "Chemically modified beta-glucuronidase crosses blood-brain barrier and clears neuronal storage in murine mucopolysaccharidosis VII," Proc Natl Acad Sci U S A, 2008, 105:2616-2621.
Hacein-Bey-Abina S, et al., "Sustained correction of X-linked severe combined immunodeficiency by ex vivo gene therapy," N Engl J Med, 2002, 346:1185-1193.
Hacein-Bey-Abina S, et al., "LMO2-associated clonal T cell proliferation in two patients after gene therapy for SCID-X1," Science, 2003, 302: 415-419.
Hacein-Bey-Abina S, et al., "Insertional oncogenesis in 4 patients after retrovirus-mediated gene therapy of SCID-X1," J Clin Invest, 2008, 118:3132-3142.
Hanenberg H, et al., "Phenotypic correction of primary Fanconi anemia T cells with retroviral vectors as a diagnostic tool," Exp Hematol, 2002; 30: 410-420.
Hansen, MS, et al., "Integration complexes derived from HIV vectors for rapid assays in vitro," Nat Biotechnol, 1999, 17: 578-582.
Hardeman MR and Ince C., "Clinical potential of in vitro measured red cell deformability, a myth?" Clin Hemorheol Microcirc, 1999, 21(3-4):277-284.
Hartung SD, et al., "Correction of metabolic, craniofacial, and neurologic abnormalities in MPS I mice treated at birth with adeno-associated virus vector transducing the human alpha-1-iduronidase gene," Mol Ther, 2004, 9:866-875.
Heilman-Miller, SL, et al., "Alteration of nucleic acid structure and stability modulates the efficiency of minus-strand transfer mediated by the HIV-1 nucleocapsid protein," J Biol Chem, 2004, 279: 44154-44165.
Herman, SA, and Coffin, JM, "Efficient packaging of readthrough RNA in ALV: implications for oncogene transduction," Science, 1987, 236: 845-848.
Higashimoto, T, et al., "The woodchuck hepatitis virus post-transcriptional regulatory element reduces readthrough transcriptions from retroviral vectors," Gene Ther, 2007, 14: 1298-1304.
Hildinger M, et al., "Design of 5' untranslated sequences in retroviral vectors developed for medical use," J Virol, 1999, 73: 4083-4089.
Hopwood and Morris, "The mucopolysaccharidoses. Diagnosis, molecular genetics and treatment," Mol Biol Med, 1999, 7:381-4041.
Horan JT, et al., "Hematopoietic stem cell transplantation for multiply transfused patients with sickle cell disease and thalassemia after low-dose total body irradiation, fludarabine, and rabbit antithymocyte globulin," Bone Marrow Transplant, 2005, 35(2):171-177.
Howe SJ, et al., "Insertional mutagenesis combined with acquired somatic mutations causes leukemogenesis following gene therapy of SCID-X1 patients," J Clin Invest, 2008, 118:3143-3150.
Huang BL, et al., "Derepression of human embryonic zeta-globin promoter by a locus-control region sequence," Proc Natl Acad Sci U S A, 1998, 95:14669-14674.
Huang S, et al., "USF1 recruits histone modification complexes and is critical for maintenance of a chromatin barrier," Mol Cell Biol, 2007, 27: 7991-8002.
Huang Y, et al., "Intronless mRNA transport elements may affect multiple steps of pre-mRNA processing," EMBO J, 1999, 18: 1642-1652.
Iannone R, et al., "Effects of mixed hematopoietic chimerism in a mouse model of bone marrow transplantation for sickle cell anemia," Blood, 2001, 97(12):3960-3965.
Iannone, R, et al., "Results of minimally toxic nonmyeloablative transplantation in patients with sickle cell anemia and betathalassemia," Biol Blood Marrow Transplant, 2003, 9(8):519-528.
Ilves, H, et al., "Retroviral vectors designed for targeted expression of RNA polymerase III-driven transcripts: a comparative study," Gene, 1996, 171: 203-208.
Imren S, et al., "Permanent and panerythroid correction of murine beta thalassemia by multiple lentiviral integration in hematopoietic stem cells," Proc Natl Acad Sci USA, 2002, 99: 14380-14385.
Julias, JG, et al., "Replication of phenotypically mixed human immunodeficiency virus type 1 virions containing catalytically active and catalytically inactive reverse transcriptase," J Virol, 2001, 75: 6537-6546.
Junker, U, et al., "Genetic instability of a MoMLV-based antisense double-copy retroviral vector designed for HIV-1 gene therapy," Gene Ther, 1995, 2: 639-646.
Junker, U, et al., "Antiviral potency of drug-gene therapy combinations against human immunodeficiency virus type 1," AIDS research and human retroviruses, 1997, 13: 1395-1402.
Kalberer CP, et al., "Preselection of retrovirally transduced bone marrow avoids subsequent stem cell gene silencing and age-dependent extinction of expression of human beta-globin in engrafted mice," Proc Natl Acad Sci USA, 2000, 97: 5411-5415.
Kalfa TA, et al., "Rac1 and Rac2 GTPases are necessary for early erythropoietic expansion in the bone marrow but not in the spleen," Haematologica, 2009, 95(1): 27-35.
Karlsson S, et al., "Expression of the human beta-globin gene following retroviral-mediated transfer into multipotential hematopoietic progenitors of mice," Proc Natl Acad Sci USA, 1988; 85: 6062-6066.
Kaye JF, et al., "cis-acting sequences involved in human immunodeficiency virus type 1 RNA packaging," J Virol, 1995, 69: 6588-6592.
Kean LS, et al., "A cure for murine sickle cell disease through stable mixed chimerism and tolerance induction after nonmyeloablative conditioning and major histocompatibility complex-mismatched bone marrow transplantation," Blood, 2002, 99(5):1840-1849.
Kean LS, et al., "Chimerism and cure: hematologic and pathologic correction of murine sickle cell disease," Blood, 2003, 102(13):4582-4593.
Kelly PF, et al., "Stem cell collection and gene transfer in fanconi anemia," MolTher, 2007, 15: 211-219.
Kennedy DW and Akowitz JL (1998), "Mature monocytic cells enter tissues and engraft," Proc Natl Acad Sci, USA 95:14944-14949.
Kim A, et al., "Distinctive signatures of histone methylation in transcribed coding and noncoding human beta-globin sequences," Mol Cell Biol, 2007, 27: 1271-1279.
Kim TH, et al., "Analysis of the vertebrate insulator protein CTCF-binding sites in the human genome," Cell, 2007, 128: 1231-1245.
Kohn DB, et al., "T lymphocytes with a normal ADA gene accumulate after transplantation of transduced autologous umbilical cord blood CD34_ cells in ADA-deficient SCID neonates," Nat Med, 1998, 4(7):775-780.
Kohn DB, et al., "Occurrence of leukaemia following gene therapy of X-linked SCID," Nature reviews, 2003, 3:477-488.
Kohn DB, "Lentiviral vectors ready for prime-time," Nat Biotechno, 2007, 25: 65-66.
Koshy M, et al., "2-deoxy 5-azacytidine and fetal hemoglobin induction in sickle cell anemia," Blood, 2000, 96(7):2379-2384.
Kraunus J, et al., "Self-inactivating retroviral vectors with improved RNA processing," Gene Ther, 2004, 11: 1568-1578.
Kraunus J, et al., "Murine leukemia virus regulates alternative splicing through sequences upstream of the 5' splice site," J Biol Chem, 2006, 281: 37381-37390.
Krishnamurti L, et al., "Bone marrow transplantation without myeloablation for sickle cell disease," N Engl J Med., 2001, 344(1): 68.
Krishnamurti L, et al., "Stable long-term donor engraftment following reduced-intensity hematopoietic cell transplantation for sickle cell disease," Biol Blood Marrow Transplant, 2008, 14(11):1270-1278.
Kumar, M. et al., "Systematic determination of the packaging limit of lentiviral vectors," Hum Gene Ther, 2001, 12: 1893-1905.

(56) References Cited

OTHER PUBLICATIONS

Kurukuti S, et al., "CTCF binding at the H19 imprinting control region mediates maternally inherited higher-order chromatin conformation to restrict enhancer access to Igf2," Proc Natl Acad Sci USA, 2006, 103: 10684-10689.

Leboulch P, et al., "Mutagenesis of retroviral vectors transducing human beta-globin gene and beta-globin locus control region derivatives results in stable transmission of an active transcriptional structure," EMBO J, 1994, 13: 3065-3076.

Levasseur DN, et al., "Correction of a mouse model of sickle cell disease: lentiviral/antisickling beta-globin gene transduction of unmobilized, purified hematopoietic stem cells," Blood, 2003, 102(13):4312-4319.

Li CL, et al., "The cHS4 chromatin insulator reduces gammaretroviral vector silencing by epigenetic modifications of integrated provirus," Gene Ther, 2008, 15: 49-53.

Litt MD, et al., "Correlation between histone lysine methylation and developmental changes at the chicken beta-globin locus," Science, 2001, 293: 2453-2455.

Litt MD, et al., "Transitions in histone acetylation reveal boundaries of three separately regulated neighboring loci," EMBO J, 2001, 20: 2224-2235.

Luban J and Goff SP, "Binding of human immunodeficiency virus type 1 (HIV-1) RNA to recombinant HIV-1 gag polyprotein," J Virol, 1991, 65: 3203-3212.

Maier-Redelsperger M, et al., "Variation in fetal hemoglobin parameters and predicted hemoglobin S polymerization in sickle cell children in the first two years of life: Parisian Prospective Study on Sickle Cell Disease," Blood, 1994, 84(9):3182-3188.

Maier-Redelsperger M, et al., "Fetal hemoglobin and F-cell responses to long-term hydroxyurea treatment in young sickle cell patients: The French Study Group on Sickle Cell Disease," Blood, 1998, 91(12):4472-4479.

Malim MH, et al., "The HIV-1 rev trans-activator acts through a structured target sequence to activate nuclear export of unspliced viral mRNA," Nature Nature, 1989, 338: 254-257.

Manci EA, et al., "Pathology of Berkeley sickle cell mice: similarities and differences with human sickle cell disease," Blood, 2006, 107(4):1651-1658.

Marcus SJ and Ware RE, "Physiologic decline in fetal hemoglobin parameters in infants with sickle cell disease: implications for pharmacological intervention," J Pediatr Hematol Oncol, 1999, 21(5): 407-411.

May C, et al., "Therapeutic haemoglobin synthesis in beta-thalassaemic mice expressing lentivirus-encoded human beta-globin," Nature, 2000, 406: 82-86.

McGrath KE, et al., "Multispectral imaging of hematopoietic cells: where flow meets morphology," J Immunol Methods, 2008, 336:91-97.

Metais JV and Dunbar CE, "The MDS1-EVI1 gene complex as a retrovirus integration site: impact on behavior of hematopoietic cells and implications for gene therapy," Mol Ther, 2008, 16:439-449.

Miller, MD, et al., "Human immunodeficiency virus type 1 preintegration complexes: studies of organization and composition," J Virol, 1997, 71: 5382-5390.

Miyoshi, H, et al., "Development of a self-inactivating lentivirus vector," J. Virol, 1998, 72: 8150-8157.

Modlich, U, et al., "Cell-culture assays reveal the importance of retroviral vector design for insertional genotoxicity," Blood, 2006, 108: 2545-2553.

Mohamedali A, et al., "Self-inactivating lentiviral vectors resist proviral methylation but do not confer position-independent expression in hematopoietic stem cells," Mol Ther, 2004, 10: 249-259.

Montini E, et al., "Hematopoietic stem cell gene transfer in a tumor-prone mouse model uncovers low genotoxicity of lentiviral vector integration," Nat Biotechnol, 2006, 24(6): 687-696.

Moreau-Gaudry F, et al., "High-level erythroid-specific gene expression in primary human and murine hematopoietic cells with self-inactivating lentiviral vectors," Blood, 2001, 98: 2664-2672.

Mutskov VJ, et al., "The barrier function of an insulator couples high histone acetylation levels with specific protection of promoter DNA from methylation," Genes Dev, 2002, 16: 1540-1554.

Neff, T., et al., "Stem cell gene therapy, position effects and chromatin insulators," Stem Cells, 1997, vol. 15, Supp. 1, pp. 265-271.

Negroni, M, and Buc, H, "Copy-choice recombination by reverse transcriptases: reshuffling of genetic markers mediated by RNA chaperones," Proc Natl Acad Sci USA, 2000, 97: 6385-6390.

Ney PA, "Gene expression during terminal erythroid differentiation," Curr Opin Hematol, 2006, 13:203-208.

Noronha PA, et al., "Hemoglobin-specific antibody in a multiply transfused patient with sickle cell disease," Blood, 1997, 89(6):2155-2158.

Novak U, et al., "High-level beta-globin expression after retroviral transfer of locus activation region-containing human beta-globin gene derivatives into murine erythroleukemia cells," Proc Natl Acad Sci USA, 1990, 87: 3386-3390.

Ohi, Y, and Clever, JL, "Sequences in the 5' and 3' R elements of human immunodeficiency virus type 1 critical for efficient reverse transcription," J Virol, 2000, 74: 8324-8334.

Ohmi K, et al., Activated microglia in cortex of mouse models of mucopolysaccharidoses I and IIIB. Proc Natl Acad Sci USA, 2003, 100:1902-1907.

Osborne, C., et al., "Amelioration of Retroviral Vector Silencing in Locus Control Region β-Globin-Transgenic Mice and Transduced F9 Embryonic Cells," J Virol., 1999, 73(7), pp. 5490-5496.

Ott MG, et al., "Correction of X-linked chronic granulomatous disease by gene therapy, augmented by insertional activation of MDS1-EVI1, PRDM16 or SETBP1," Nat Med, 2006, 12: 401-409.

Pan D, et al., "Retroviral vector design studies toward hematopoietic stem cell gene therapy for mucopolysaccharidosis type I," Gene Ther, 2000, 7:1875-1883.

Pan D, et al., "Biodistribution and toxicity studies of VSVG-pseudotyped lentiviral vector after intravenous administration in mice with the observation of in vivo transduction of bone marrow," Mol Ther, 2002, 6:19-29.

Pan D, et al., "Improved gene transfer and normalized enzyme levels in primitive hematopoietic progenitors from patients with mucopolysaccharidosis type I using a bioreactor," J Gene Med, 2004, 6:1293-1303.

Pan D, et al., "Progression of multiple behavioral deficits with various ages of onset in a murine model of Hurler syndrome," Brain Res, 2008, 1188:241-253.

Pannell D, et al., "Retrovirus vector silencing is de novo methylase independent and marked by a repressive histone code," EMBO J, 2000, 19: 5884-5894.

Pant V, et al., "Mutation of a single CTCF target site within the H19 imprinting control region leads to loss of Igf2 imprinting and complex patterns of de novo methylation upon maternal inheritance," Mol Cell Biol, 2004, 24: 3497-3504.

Parelho V, et al., "Cohesins functionally associate with CTCF on mammalian chromosome arms," Cell, 2008, 132: 422-433.

Parolin C, et al., "Analysis in human immunodeficiency virus type 1 vectors of cis-acting sequences that affect gene transfer into human lymphocytes," J Virol, 1994, 68: 3888-3895.

Pászty C, et al., "Transgenic knockout mice with exclusively human sickle hemoglobin and sickle cell disease," Science, 1997, 278(5339):876-878.

Pathak VK, et al., "Broad spectrum of in vivo forward mutations, hypermutations, and mutational hotspots in a retroviral shuttle vector after a single replication cycle: deletions and deletions with insertions," Proc Natl Acad Sci USA, 1990, 87: 6024-6028.

Pawliuk R, et al., "Correction of sickle cell disease in transgenic mouse models by gene therapy," Science, 2001, 294(5550):2368-2371.

Persons DA, et al., "The degree of phenotypic correction of murine beta-thalassemia intermedia following lentiviral-mediated transfer of a human gamma-globin gene is influenced by chromosomal position effects and vector copy number," Blood, 2003, 101: 2175-2183.

(56) References Cited

OTHER PUBLICATIONS

Perumbeti, A., et al., "A novel human gamma-globin gene vector for genetic correction of sickle cell anemia in a humanized sickle mouse model: critical determinants for successful correction," Blood, 2009, vol. 114, pp. 1174-1185.

Pestina TI, et al., "Correction of murine sickle cell disease using gamma-globin lentiviral vectors to mediate high-level expression of fetal hemoglobin," Mol Ther, 2009,17(2):245-252.

Peters C, et al., "Outcome of unrelated donor bone marrow transplantation in 40 children with Hurler syndrome," Blood, 1996, 87:4894-4902.

Pikaart MJ, et al., "Loss of transcriptional activity of a transgene is accompanied by DNA methylation and histone deacetylation and is prevented by insulators," Genes Dev, 1998, 12: 2852-2862.

Platt OS, et al., "Mortalit in sickle cell disease: life expectancy and risk factors for early death," N Engl J Med, 1994, 330(23):1639-1644.

Plavec I, et al., "A human beta-globin gene fused to the human beta-globin locus control region is expressed at high levels in erythroid cells of mice engrafted with retrovirus-transduced hematopoietic stem cells," Blood, 1993, 81: 1384-1392.

Puthenveetil and Malik, "Gene therapy for hemoglobinopathies: are we there yet?" Curr Hematol Rep 2004; 3: 298-305

Puthenveetil G, et al., "Successful correction of the human beta-thalassemia major phenotype using a lentiviral vector," Blood, 2004, 104: 3445-3453.

Ramezani, A, et al., "Performance- and safety-enhanced lentiviral vectors containing the human interferon-beta scaffold attachment region and the chicken beta-globin insulator," Blood, 2003, 101: 4717-4724.

Recillas-Targa, F, et al., "Positional enhancer-blocking activity of the chicken beta-globin insulator in transiently transfected cells," PNAS, 1999, 96: 14354-14359.

Recillas-Targa F, et al., "Position-effect protection and enhancer blocking by the chicken beta-globin insulator are separable activities," Proc Natl Acad Sci USA, 2002, 99: 6883-6888.

Richardson JH, et al., "Packaging of human immunodeficiency virus type 1 RNA requires cis-acting sequences outside the 5' leader region," J Virol, 1993, 67: 3997-4005.

Rivella S, et al., "The cHS4 insulator increases the probability of retroviral expression at random chromosomal integration sites," J Virol, 2000, 74: 4679-4687.

Rivella, S, et al., "A novel murine model of Cooley anemia and its rescue by lentiviral-mediated human beta-globin gene transfer," Blood, 2003, 101: 2932-2939.

Roces DP, et al., "Efficacy of enzyme replacement therapy in alpha-mannosidosis mice: a preclinical animal study," Hum Mol Genet, 2004, 13:1979-1988.

Rubin JE, et al., "Locus control region activity by 5HS3 requires a functional interaction with beta-globin gene regulatory elements: expression of novel beta/ gamma-globin hybrid transgenes," Blood, 2000, 95(10):3242-3249.

Ryu BY, et al., "A chromatin insulator blocks interactions between globin regulatory elements and cellular promoters in erythroid cells," Blood Cells Mol Dis, 2007, 39: 221-228.

Ryu BY, et al., "An experimental system for the evaluation of retroviral vector design to diminish the risk for proto-oncogene activation," Blood, 2008, 111: 1866-1875.

Sabatino, DE, et al., "Long-term expression of gamma-globin mRNA in mouse erythrocytes from retrovirus vectors containing the human gamma globin gene fused to the ankyrin-1 promoter," PNAS, 2000, 97: 13294-13299.

Sabatino, DE, et al., "A Minimal Ankyrin Promoter Linked to a Human gamma-Globin Gene Demonstrates Erythroid Specific Copy Number Dependent Expression with Minimal Position or Enhancer Dependence in Transgenic Mice," J Biol Chem, 2000, 15: 28549-28554.

Sadelain M, et al., "Generation of a high-titer retroviral vector capable of expressing high levels of the human beta-globin gene," Proc Natl Acad Sci USA, 1995, 92: 6728-6732.

Saitoh N, et al., "Structural and functional conservation at the boundaries of the chicken beta-globin domain," EMBO J, 2000, 19: 2315-2322.

Samakoglu S, et al., "A genetic strategy to treat sickle cell anemia by coregulating globin transgene expression and RNA interference," Nat Biotechnol, 2006, 24(1):89-94.

Schambach A, et al., "Overcoming promoter competition in packaging cells improves production of self-inactivating retroviral vectors," Gene Ther, 2006, 13: 1524-1533.

Schambach, A, et al., "Improving a transcriptional termination of self-inactivating gamma-retroviral and lentiviral vectors," Mol Ther, 2007, 15: 1167-1173.

Schwartz S, et al., "Mutational inactivation of an inhibitory sequence in human immunodeficiency virus type 1 results in Rev-independent gag expression," J Virol, 1992, 66: 7176-7182.

Scott HS, et al., "Human alpha-L-iduronidase: cDNA isolation and expression," Proc Natl Acad Sci USA, 1991, 88:9695-9699.

Shang Y, et al, "Cofactor dynamics and sufficiency in estrogen receptor-regulated transcription," Cell, 2000 103: 843-852.

Shin, NH, et al., "Replication of lengthened Moloney murine leukemia virus genomes is impaired at multiple stages," J Virol, 2000, 74: 2694-2702.

Sly WS, et al., "Enzyme therapy in mannose receptor-null mucopolysaccharidosis VII mice defines roles for the mannose 6-phosphate and mannose receptors," Proc Natl Acad Sci USA, 2006, 103:15172-15177.

Smith ST, et al., "Genome wide ChIP-chip analyses reveal important roles for CTCF in *Drosophila* genome organization," Dev Biol, 2009, 328: 518-528.

Socolovsky M, et al., "Ineffective erythropoiesis in Stat5a(-/-)5b(-/-) mice due to decreased survival of early erythroblasts," Blood, 2001, 98:3261-3273.

Souillet G, et al., "Outcome of 27 patients with Hurler's syndrome transplanted from either related or unrelated haematopoietic stem cell sources," Bone Marrow Transplant, 2003, 31:1105-1117.

Splinter E, et al., "CTCF mediates long-range chromatin looping and local histone modification in the beta-globin locus," Genes Dev, 2006, 20: 2349-2354.

Staba SL, et al., "Cord-blood transplants from unrelated donors in patients with Hurler's syndrome," N Engl J Med, 2004, 350:1960-1969.

Steinberg MH, et al., "Effect of hydroxyurea on mortality and morbidity in adult sickle cell anemia: risks and benefits up to 9 years of treatment," JAMA. 2003;289(13):1645-1651.

Stumph WE, et al., "Genomic structure and possible retroviral origin of the chicken CR1 repetitive DNA sequence family," Proc Natl Acad Sci, USA, 1984, 81: 6667-6671.

Sundquist WI, Heaphy S, "Evidence for interstrand quadruplex formation in the dimerization of human immunodeficiency virus 1 genomic RNA," Proc Natl Acad Sci USA, 1993, 90: 3393-3397.

Surinya KH, et al., "Identification and characterization of a conserved erythroid-specific enhancer located in intron 8 of the human 5-aminolevulinate synthase 2 gene," J Biol Chem, 1998, 273:16798-16809.

Swanson, C., et al., "Retroviral mRNA nuclear export elements regulate protein function and virion assembly," Embo J., 2004, 23: 2632-2640.

Thrasher, AJ, et al., "Gene therapy X-SCID transgene leukaemogenicity," Nature, 2006, 443: E5-E6.

Topping, R, et al., "Cis-acting elements required for strong stop acceptor template selection during Moloney imurine leukemia virus reverse transcription," J Mol Biol, 1998, 281: 1-15.

Trudel M, et al., "Sickle cell disease of transgenic SAD mice," Blood, 1994, 84(9):3189-3197.

Urbinati, F., et al., "Mechanism of reduction in titers from lentivirus vectors carrying large inserts in the 3'LTR," Molecular Therapy, 2009, vol. 17(9), pp. 1527-1536.

Vogler C, et al., "Overcoming the blood-brain barrier with high-dose enzyme replacement therapy in murine mucopolysaccharidosis VII," Proc Natl Acad Sci USA, 2005, 102:14777-14782.

Von Kalle C, et al., "Lenti in red: progress in gene therapy for human hemoglobinopathies," *J Clin Inves,* 2004, 114:889-891.

(56) References Cited

OTHER PUBLICATIONS

Wallace JA, et al., "We gather together: insulators and genome organization," Curr Opin Genet Dev, 2007, 17: 400-407.
Walters MC, et al., "Barriers to bone marrow transplantation for sickle cell anemia," Biol Blood Marrow Transplant, 1996, 2(2): 100-104.
Walters MC, et al., "Stable mixed hematopoietic chimerism after bone marrow transplantation for sickle cell anemia," Biol Blood Marrow Transplant, 2001, 7(12):665-673.
Wang, D., et al., "Reprogramming erythroid cells for lysosomal enzyme production leads to visceral and CNS cross-correction in mice with Hurler syndrome," PNAS, 2009, vol. 106(47), pp. 19958-19963.
Wendt KS, et al., "Cohesin mediates transcriptional insulation by CCCTC-binding factor," Nature, 2008, 451: 796-801.
West AG, et al., "Recruitment of histone modifications by USF proteins at a vertebrate barrier element," Mol Cell, 2004, 16: 453-463.
Williams A, et al., "The role of CTCF in regulating nuclear organization," J Exp Med, 2008, 205: 747-750.
Wiznerowicz, M, et al., "Double-copy bicistronic retroviral vector platform for gene therapy and tissue engineering: application to melanoma vaccine development," Gene Ther, 1997, 4: 1061-1068.
Wiznerowicz, M, et al., "Development of a double-copy bicistronic retroviral vector for human gene therapy," Advances in experimental medicine and biology, 1998, 451: 441-447.
World Health Organization, "Sickle-Cell Anaemia Fifty-Ninth World Health Assembly," Provisional Agenda Item 11.4., 2006, A59:1.
Worsham DN, et al., "In vivo gene transfer into adult stem cells in unconditioned mice by in situ delivery of a lentiviral vector," Mol Ther, 2006, 14:514-524.
Wu, T, et al., "Effects of nucleic acid local structure and magnesium ions on minus-strand transfer mediated by the nucleic acid chaperone activity of HIV-1 nucleocapsid protein," Nucleic Acids Res, 2007, 35: 3974-3987.
Xie X, et al., "Systematic discovery of regulatory motifs in conserved regions of the human genome, including thousands of CTCF insulator sites," Proc Natl Acad Sci USA, 2007, 104: 7145-7150.
Yanez-Munoz, RJ, et al., "Effective gene therapy with nonintegrating lentiviral vectors," Nature medicine, 2006, 12: 348-353.
Yannaki E, et al., "Topological constraints governing the use of the chicken HS4 chromatin insulator in oncoretrovirus vectors," Mol Ther, 2002, 5: 589-598.
Yao S, et al., "Retrovirus silencer blocking by the cHS4 insulator is CTCF independent," Nucleic Acids Res, 2003, 31: 5317-5323.
Yu SS, et al., "Construction of a retroviral vector production system with the minimum possibility of a homologous recombination," Gene Ther, 2003, 10: 706-711.
Yusufzai TM and Felsenfeld G, "The 5'-HS4 chicken beta-globin insulator is a CTCF-dependent nuclear matrix-associated element," Proc Natl Acad Sci USA, 2004, 101: 8620-8624.
Yusufzai TM, et al., "CTCF tethers an insulator to subnuclear sites, suggesting shared insulator mechanisms across species," Mol Cell, 2004, 13: 291-298.
Zaiss, AK, et al., "RNA 3' readthrough of oncoretrovirus and lentivirus: implications for vector safety and efficacy," J Virol, 2002, 76: 7209-7219.
Zennou, V, et al., "HIV-1 genome nuclear import is mediated by a central DNA flap," Cell, 2000, 101: 173-185.
Zhao KW, et al., "Carbohydrate structures of recombinant human alpha-L-iduronidase secreted by Chinese hamster ovary cells," J Biol Chem, 1997, 272:22758-22765.
Zhuang J, et al., "Human immunodeficiency virus type 1 recombination: rate, fidelity, and putative hot spots," J Virol, 2002, 76: 11273-11282.
Zufferey R, et al., "Self-inactivating lentivirus vector for safe and efficient in vivo gene delivery," J Virol. 1998, 72: 9873-9880.
Zychlinski D, et al., "Physiological promoters reduce the genotoxic risk of integrating gene vectors," Mol Ther, 2008, 16: 718-725.
Di Domenico et al., "Gene Therapy for a Mucopolysaccharidosis Type I Murine Model with Lentiviral-IDUA Vector," Hum. Gene Ther., Jan. 2005, pp. 81-90 (12 pgs.), vol. 16(1).

* cited by examiner

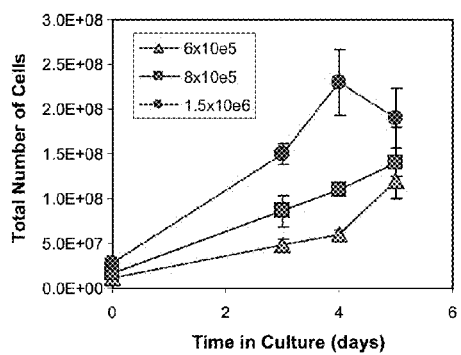
Figure 1A
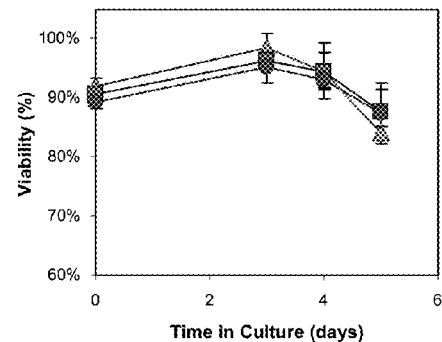
Figure 1B
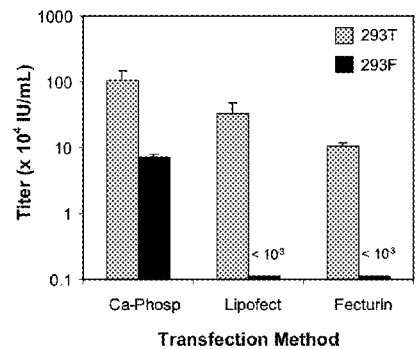
Figure 2A
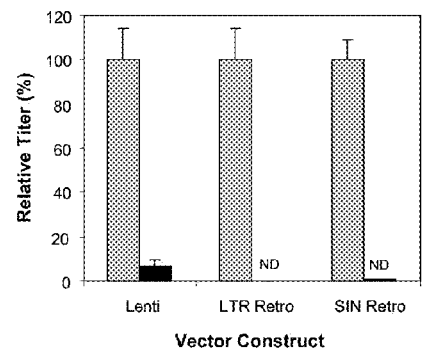
Figure 2B
| Time of Transfection | Titer HT1080 (x 10$^5$ IU/mL) | | | | |
|---|---|---|---|---|---|
| | H1 | H2 | H3 | H4 | H5 |
| 1 day post-seeding | <0.1 | <0.1 | <0.1 | <0.1 | <0.1 |
| 4 hours post-seeding | 4.3 | 2.4 | 1.8 | 1.2 | 0.4 |
Figure 3

METHODS OF IMPROVING RETROVIRAL TITER IN TRANSFECTION-BASED PRODUCTION SYSTEM USING EUKARYOTIC CELLS

CROSS REFERENCE TO RELATED APPLICATIONS

This non-provisional application is a continuation of and claims priority from U.S. Non-Provisional application Ser. No. 12/928,302, filed on Dec. 6, 2010, which in turn claims priority to U.S. Provisional Application No. 61/267,008, filed on Dec. 4, 2009, both of which are herein incorporated by reference in their entirety.

FIELD OF THE INVENTION

The invention disclosed herein generally relates to methods of improving titer in transfection-based bioreactor culture production or transfection-based production systems using a eukaryotic cell.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Improvement of Viral Titer

Significant research has been devoted to improving viral titer by manipulating the parameters of production in closed system bioreactors. Increases in titer translate into practical benefits, including decreased costs and the related potential for expanding the patient base for clinical trials. Thus, there is a continued need in the art for improving titer by optimizing the parameters of bioreactor vector production.

SUMMARY OF THE INVENTION

Methods and composition described herein are provided by way of example and should not in any way limit the scope of the invention.

In one aspect, a method of improving viral titer in transfection-based production system using a eukaryotic cell is provided. The method comprises at least one of: harvesting a population of eukaryotic cells prior to transfection that have progressed beyond log phase of cell growth to a state of confluency for at least 24 hours; mixing the population with transfection reagents and plasmid DNA at the time of re-seeding into a new culture vessel, where the harvesting and mixing steps, alone or in combination, results in an improved viral titer, by at least 2-fold, in a transfection-based production using a eukaryotic cell.

In another aspect, a method of improving titer in transfection-based production using a eukaryotic cell is provided. The method comprises at least one of: harvesting of a confluent population of eukaryotic cells for transfection that have progressed beyond log phase of growth; mixing the population with transfection reagents and plasmid DNA at the time of seeding; and seeding cells at a cell density of at least $5\times10^4$ cells/cm$^2$ 4 to 5 days prior to cell harvest and transfection, where any of the harvesting, mixing, and/or seeding, alone or in any combination, results in an improved titer, by at least 2-fold, in a transfection-based production using a eukaryotic cell.

In another aspect, a method of improving titer in transfection-based bioreactor culture production using a eukaryotic cell is provided. The method comprises at least one of: harvesting of a confluent population of eukaryotic cells for transfection that have progressed beyond log phase of growth; mixing the population with transfection reagents and plasmid DNA at the time of seeding; seeding cells at a cell density of at least $5\times10^4$ cells/cm$^2$ 4 to 5 days prior to cell harvest and transfection; and transfecting of cells with at least 9.2 μg/ml of plasmid DNA, using either suspension cells or cells to be plated onto carriers or microcarriers, wherein any of the harvesting, mixing, seeding, and/or transfecting steps, alone or in any combination, results in an improved titer, by at least 2-fold, in transfection-based bioreactor culture production using a eukaryotic cell.

BRIEF DESCRIPTION OF THE FIGURES

Those of skill in the art will understand that the drawings, described below, are for illustrative purposes only. The drawings are not intended to limit the scope of the present teachings in any way.

FIG. 1 depicts expansion (A) and cell viability (B) of 293F cell suspension culture over time when initiated at $6\times10^5$, $8\times10^5$, and $1.5\times10^6$ c/mL; mean±SD (n=3).

FIG. 2 depicts titer of MIEG3 (RD114) produced on 293T and 293F cells transfected using different transfection methods (A); and relative titer of a lentivirus and gammaretrovirus (LTR and SIN configuration) transfected with lipofectamine (B); mean±SD (n=2). ND, not detected.

FIG. 3 depicts 293T cells ($2.5\times10^8$) were transfected in a 500 mL FibraStage culture system (New Brunswick Scientific; disposable 500 mL bottle with FibraCel mounted on a movable stage) with 500 microgram of SRS11.SF.GFP.pre*SE, 450 microgram of pCDNA3.MLV.g/p and 200 microgram of GALV envelope plasmid using Calcium Phosphate. One group was transfected at the time of seeding (4 hours post-seeding), the other group was transfected the day after seeding.

DESCRIPTION OF THE INVENTION

Figure 4:
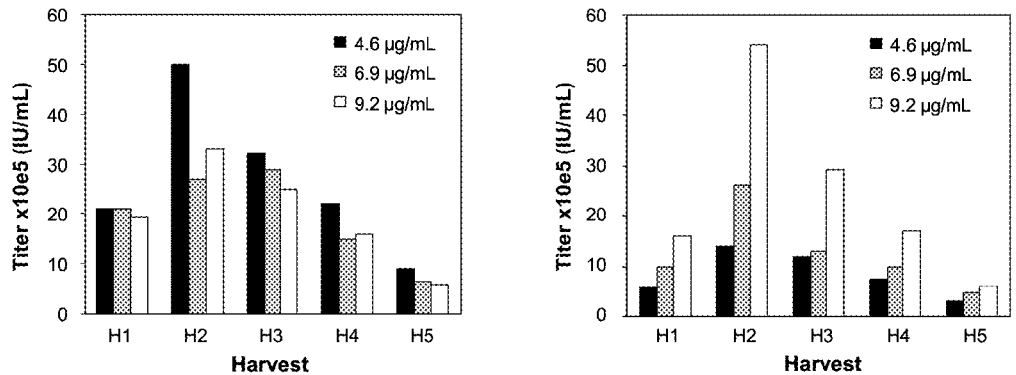
FIG. 4 depicts 293T cells were transfected on tissue culture plastic ($2\times10^7$ cells per T75 in 10 mL D10) or on FibraCel ($2\times10^8$ cells per 2 gram in 100 mL D10) with SRS11.SF.DsRed2.pre*, pCDNA3.MLV.gp, and Eco-env using different amounts of plasmid DNA (total amount expressed as μg per mL of media). Vector was harvested at 12-hour intervals and titered on NIH 3T3.

Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the term "293F" is a designation of a cell line.

As used herein, the term "293T" is a designation of a cell line.

As used herein, the term "3T3" is a designation of a cell line.

As used herein, the term "cDNA" is an abbreviation of complimentary DNA.

As used herein, the term "cGMP" as it relates to virus production is an abbreviation of current good manufacturing practice.

As used herein, the term "D10" is an abbreviation of DMEM medium containing 10% of fetal bovine serum.

As used herein, the term "DMEM" is an abbreviation of a tissue culture medium, Dulbecco's Modified Eagles Medium.

As used herein, the term "DNA" is an abbreviation of Deoxyribonucleic Acid.

As used herein, the term "Eco" is an abbreviation of the Ecotropic envelope protein.

As used herein, the term "Env" is an abbreviation of an envelope protein.

As used herein, the term "FBS" is an abbreviation of fetal bovine serum.

As used herein, the term "GALV" is an abbreviation of the Gibbon Ape Leukemia Virus envelope.

As used herein, the term "GFP" is an abbreviation of green fluorescent protein.

As used herein, the term "HEK293" is a designation of a cell line.

As used herein, the term "HIV" is an abbreviation of human immunodeficiency virus.

As used herein, the term "HT1080" is a designation of a cell line.

As used herein, the term "LRF" is an abbreviation of Leukocyte Reduction Filter.

As used herein, the term "LTR" is an abbreviation of long terminal repeat.

As used herein, the term "MCB" is an abbreviation of Master Cell Bank.

As used herein, the term "MIEG3" is a designation of a gamma-retroviral vector.

As used herein, the term "NIH" is an abbreviation of National Institutes of Health.

As used herein, the term "NTP" is an abbreviation of national toxicology program.

As used herein, the term "PBS" is an abbreviation of Phosphate-Buffered Saline.

As used herein, the term "pCDNA3.MLV.g/p" is a designation of a plasmid containing packaging sequences.

As used herein, the term "RD114" is an abbreviation of the feline leukemia virus envelope.

As used herein, the term "SERS11.EGFP.pre*" is a designation of a gamma-retroviral vector.

As used herein, the term "SIN" is an abbreviation of self-inactivating.

As used herein, the term "SIN11.SF.eGFP.pre*" is a designation of a gamma-retroviral vector.

As used herein, the term "SRS11.EFS.IL2RGpre*" is a designation of a gamma-retroviral vector.

As used herein, the term "SRS11.SF.DsRed2.pre*" is a designation of a gamma-retroviral vector.

As used herein, the term "SRS11.SF.GFP.pre*SE" is a designation of a gamma-retroviral vector.

As used herein, the term "T225" is an abbreviation of a 225 $cm^2$ tissue culture flask.

As used herein, the term "T75" is an abbreviation of a 75 $cm^2$ tissue culture flask.

Improved Vector Production

As disclosed herein, the need for clinical grade gamma-retroviral vectors with self-inactivating (SIN) long terminal repeats has prompted a shift in the method with which large scale cGMP-grade vectors are produced, from the use of stable producer lines to transient transfection-based techniques. A method was developed based on the Wave Bioreactor® (GE Healthcare) production platform. This platform allows for large-scale closed-system production of high-titer retroviral vectors for clinical trials using transient transfection up to 25 Liters per harvest using closed system processing. The present application describes the development and scale-up procedures and reports on the successful use of the Wave Bioreactor in the production of six cGMP grade retroviral vectors in support of the FDA's National Toxicology Program (NTP).

As further disclosed herein, in order to determine the optimal time of transfection, 293T cells were seeded onto FibraCel and exposed to transfection reagents and plasmid DNA within hours of seeding as compared to cells that were transfected the following day. The data show a titer of less than $10^4$ IU/mL from cells that were transfected one day post-seeding as compared to cells that were transfected the same day. It has now been determined that optimal titers are achieved when cells are mixed with transfection reagents and plasmid DNA at the time of seeding onto FibraCel. Cells were plated at different cell densities, harvested and tested for virus production in five separate experiments using GALV pseudotyped gamma-retroviral vectors. Although the same number of cells was used for each group, titers varied greatly based on the plating density and were higher when cells were harvested from plates that had been seeded with a higher cell density. For scale-up, several parameters were tested including the time of media change post-transfection and the length of time the cells were exposed to PBS and TrypLESelect prior to transfection. To establish the amount of plasmid DNA necessary to improve titer, 293T cells were transfected side-by-side on tissue culture plastic as well as FibraCel. Where increasing plasmid DNA in static cultures produced a lower titer, increasing the DNA concentration on FibraCel increased titer.

In one embodiment, the present invention provides a method of improving viral titer in a transfection-based production system using eukaryotic cells. In another embodiment, the cells harvested prior to transfection have progressed beyond log phase of cell growth. In another embodiment the cells have achieved a state of confluency for at least 24 hours. In another embodiment, the cells are seeded at a cell density of at least $5 \times 10^4$ 4 to 5 days prior to cell harvest and transfection. In another embodiment the cells are mixed with transfection reagents and plasmid DNA at the time of re-seeding into a new culture vessel. In another embodiment, the plasmid concentration used for transfection is at least 7 μg/ml of plasmid DNA. In another embodiment, the plasmid concentration used for transfection is at least 9.2 μg/ml of plasmid DNA. In another embodiment, the media is changed 12-24 hours post-transfection. In another embodiment, the media is changed 14-20 hours post-transfection. In another embodiment, the media is changed 19 hours post-transfection. In another embodiment, cells are rinsed with PBS followed by 3-8 minute exposure to TrypLESelect prior to transfection. In another embodiment, cells are rinsed with PBS followed by 4-7 minute exposure to TrypLESelect prior to transfection. In another embodiment, cells are rinsed with PBS followed by 5 minute exposure to TrypLESelect prior to transfection. In another embodiment, the harvesting, mixing, re-seeding, and/or transfection steps, alone or in combination, results in improved viral titer compared to traditional protocols of transfection-based production using eukaryotic cells. In another embodiment, the cells are 293T cells. In another embodiment, the vector is a SIN lentiviral vector. In another embodiment, the vector is a Gamma-Retroviral vector. In another embodiment, the vector is a SIN Gamma-retroviral vector. In another embodiment, the retroviral vectors produced are cGMP grade vectors. In another embodiment, the vectors are produced in a closed system bioreactor.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Optimizing Closed-System Production of High-Titer Retroviral Vectors

The need for clinical grade gamma-retroviral vectors with self-inactivating (SIN) long terminal repeats has prompted a shift in the method with which large scale cGMP-grade vectors are produced, from the use of stable producer lines to transient transfection-based techniques. The Vector Production Facility, an academic cGMP manufacturing laboratory that is part of the Translational Core Laboratories at the Cincinnati Children's Research Foundation, has developed such a method based on the Wave Bioreactor® (GE Healthcare) production platform. This platform allows for large scale closed-system production of high-titer retroviral vectors for clinical trials using transient transfection up to 25 Liters per harvest using closed system processing.

The present study describes the development and scale-up procedures and reports on the successful use of the Wave Bioreactor in the production of six cGMP grade retroviral vectors in support of the FDA's National Toxicology Program (NTP).

Example 2

Transfection

Adherent 293T cells were transfected in T75 or T225 flasks or on 2 gram of FibraCel discs in ridged 850 $cm^2$ roller bottles (10 mL/T75; 30 mL/T225; 100 mL/roller bottle). Non-adherent 293F cells were grown in suspension culture and transfected in either serum-free FreeStyle 293 media (non-adherent conditions), or in FreeStyle media or DMEM supplemented with FBS (adherent conditions) in tissue culture flasks. Transfections were done using Calcium Phosphate (adherent conditions only), Lipofectamine 2000, or Fecturin according to the manufacturer's instructions. Vector was collected at 12 or 24 hour intervals, filtered at 0.45 μm, and frozen at or below −70° C. In the Bioreactor (suspension cells or adherent cells on Fibracel), higher titers were obtained when a higher concentration of plasmid was utilized (9.2 performed better than 6.9 or 4.6 microgram of total plasmid/mL media). Higher concentrations were not tested but may result in even further enhancements.

Example 3

Large Scale Virus Production

Cells from a certified 293T master cell bank (MCB) were expanded on tissue culture plastic, harvested, mixed with calcium phosphate transfection reagents and plasmid (4 g vector, 3.6 gram gag/pol, 1.6 gram env per Liter), and pumped into a Wave Cell Bag (GE Healthcare) containing FibraCel® discs (New Brunswick) in DMEM with 10% FBS (D10). Cells were cultured at 37° C., 5% CO2 using a rocking speed of 22 rpm and 6° angle. At 16-20 hours post-transfection, the media was exchanged; virus was harvested at approximately 12-hour intervals, filtered through a leukocyte reduction filter (Pall), aliquoted into Cryocyte freezing containers using a closed system fluid path, placed in protective freezing cassettes and frozen at or below −70° C.

Example 4

Titration

Vector pseudotyped with an ecotropic envelope was titered on NIH 3T3 cells, vector pseudotyped with the Gibbon Ape Leukemia (GALV) or Feline Leukemia Virus (RD114) envelope was titered on HT1080 cells. Titers were calculated based on the % GFP expression as determined by FACS or based on copy number as determined by vector specific quantitative PCR.

Example 5

Suspension Culture

Initial pilot studies and scale-up were done with HEK293-derived 293F cells (Invitrogen) grown in serum-free (SF)

FreeStyle 293 media (Invitrogen) as suspension cells are easier to manipulate in a bioreactor. Studies show up to 10-fold expansion over 5 days with cell viability at or above 80% (FIG. 1). However, 293F cells produced a 20-fold lower titer when transfected under adherent conditions in D10 with Ca-Phosphate (FIG. 2) and no detectable titer with other transfection reagents or under non-adherent conditions.

Example 6

Adherent Cell Culture

FibraCel disks (New Brunswick Scientific) are available as a sterile pre-loaded substrate for the Wave Bioreactor (at 20 gram per Liter) to support growth of adherent cells. Small scale pilot studies using adherent 293T cells were performed in 850 cm$^2$ ridged roller bottles with 2 gram FibraCel discs per 2×10$^8$ 293T cells per 100 mL of D10. Post-seeding, cells migrate inside of the matrix and continue to expand as can be determined by glucose consumption over time. Glucose levels in a 1 Liter bioreactor that had been seeded with 2×10$^9$ transfected 293T cells showed that the media should be changed at approximately 12 hour intervals to maintain a glucose level above 100 mg/dL. Treatment with TrypLESelect for up to 30 minutes allows up to 20% of the post-production cells to be released and harvested while the majority of cells maintain trapped in the matrix.

Example 7

Time of Transfection

To determine the optimal time of transfection, 293T cells were seeded onto FibraCel and exposed to transfection reagents and plasmid DNA within hours of seeding as compared to cells that were transfected the following day. The data show a titer of less than 10$^4$ IU/mL from cells that were transfected one day post-seeding as compared to cells that were transfected the same day (FIG. 3). It has now been determined that optimal titers are achieved when cells are mixed with transfection reagents and plasmid DNA at the time of seeding onto FibraCel.

Example 8

Plasmid DNA

To establish the amount of plasmid DNA needed for optimal titer, 293T cells were transfected side-by-side on tissue culture plastic as well as on FibraCel. Where increasing plasmid DNA in static cultures produced a lower titer, increasing the DNA concentration on FibraCel increased titer as shown in a representative dataset (FIG. 4) our of a total of 3 experiments.

Example 9

Cell Culture

Figure 5A:
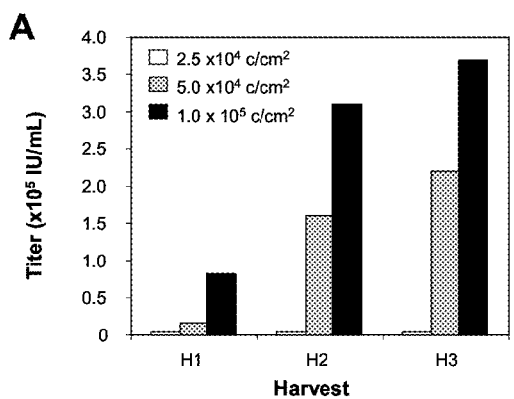
FIG. 5 depicts 293T cells were plated at a cell density of $2.5\times10^4$, $5\times10^4$, and $1\times10^5$ cells/cm$^2$ 4 days prior to transfection. At the day of transfection, cells were harvested and $2\times10^8$ cells from each group were transfected with a GALV pseudotyped SIN11.SF.eGFP.pre* (A) and SRS11.EFS.IL2RGpre* (B). Vector was harvested at 12-hour intervals and titered on HT1080.
Figure 5B:
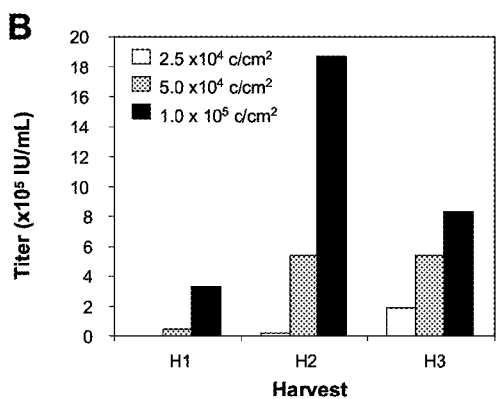

Cells were plated at different cell densities (from 2.5×10$^4$ cells/cm$^2$ through 1×10$^5$ cells/cm$^2$) 4 days prior to transfection, harvested and tested for virus production in five separate experiments using GALV pseudotyped gamma-retroviral vectors. Although the same number of cells was used for each group, titers on plastic surface as well as on Fibracel cultures in the bioreactor varied greatly based on the plating density and were higher when cells were harvested from plates that had been seeded with a higher cell density (>2.5×10$^4$ cells/cm$^2$) (FIG. 5).

Example 10

Scale-Up

Figure 6A:
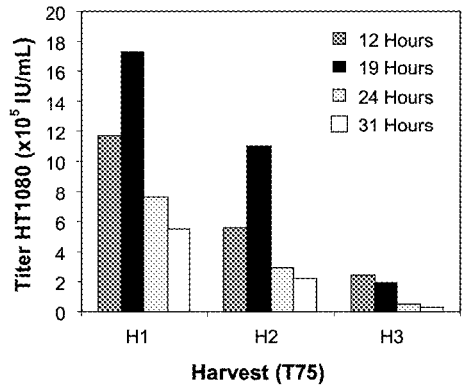
FIG. 6 depicts 293T cells were transfected T75 ($2\times10^7$ cells per flask in 10 mL D10) with SERS11.EGFP.pre*, pCDNA3.MLV.gp, and GALV-env. Post-transfection, media was changed at various time points (A). Comparison of PBS rinse followed by 5 min exposure of TrypLESelect and exposure to PBS for 20 min and exposure to TrypLESelect for 30 min, all groups showed >95% viability (B). Average±SD (n=2).
Figure 6B:
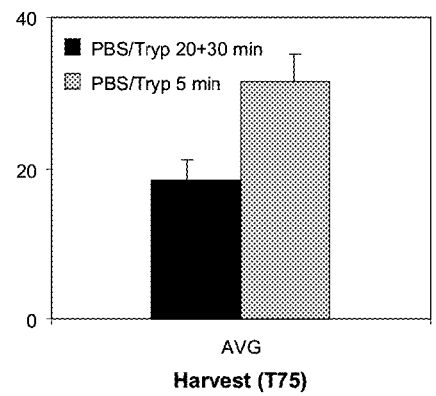

Several parameters were tested including the time of media change post-transfection (FIG. 6A) and the length of time cells were exposed to PBS and TrypLESelect prior to transfection (FIG. 6B). For media change, 19 hours was found to be optimal in two separate experiments (representative experiment shown). Although all cells had >95% viability after exposure to PBS and TrypLESelect, cells exposed for a shorter period of time generated higher titers.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the specific number of genes or targeted by a therapeutic product, the type of gene, the type of genetic disease or deficiency, and the gene(s) specified. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of improving retroviral titer in a transfection-based production system using a population of eukaryotic cells, the method comprising: (i) seeding a population of eukaryotic cells at a cell density of at least $5 \times 10^4$ cells/cm$^2$ 4 to 5 days prior to cell harvest; (ii) harvesting the population of eukaryotic cells, wherein the population of eukaryotic cells has progressed beyond log phase of cell growth to a state of confluency for at least 24 hours; and (iii) mixing the population of eukaryotic cells harvested in (ii) with a transfection reagent and a retroviral vector at the time of re-seeding the population of eukaryotic cells into a culture vessel.

2. The method of claim 1, further comprising contacting the population of eukaryotic cells harvested in step (ii) to a protease elect prior to step (iii).

3. The method of claim 2, wherein the contacting step is performed by incubating the population of eukaryotic cells with a protease for 3-8 minutes prior to step (iii).

4. The method of claim 2, wherein the contacting step is performed by incubating the population of eukaryotic cells with a protease for 4-7 minutes prior to step (iii).

5. The method of claim 2, wherein the contacting step is performed by incubating the population of eukaryotic cells with a protease for 5 minutes prior to transfection.

* * * * *